(12) United States Patent
Rolfes Meyering

(10) Patent No.: US 8,568,760 B2
(45) Date of Patent: Oct. 29, 2013

(54) HYDROPHOBIC POLYSACCHARIDES WITH PENDENT GROUPS HAVING TERMINAL REACTIVE FUNCTIONALITIES AND MEDICAL USES THEREOF

(75) Inventor: Emily R. Rolfes Meyering, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 32 days.

(21) Appl. No.: 12/982,214

(22) Filed: Dec. 30, 2010

(65) Prior Publication Data

US 2011/0159067 A1 Jun. 30, 2011
US 2012/0052107 A9 Mar. 1, 2012

Related U.S. Application Data

(60) Provisional application No. 61/291,172, filed on Dec. 30, 2009.

(51) Int. Cl.
*A61F 13/00* (2006.01)
*C07H 1/00* (2006.01)

(52) U.S. Cl.
USPC ........................................ 424/422; 536/123.1

(58) Field of Classification Search
USPC ........................................ 424/422; 536/123.1
See application file for complete search history.

(56) References Cited

U.S. PATENT DOCUMENTS

| | | | |
|---|---|---|---|
| 4,011,392 A | 3/1977 | Rudolph et al. | |
| 5,459,258 A | 10/1995 | Merrill et al. | |
| 5,470,581 A | 11/1995 | Grillo et al. | |
| 5,869,647 A | 2/1999 | Narayan et al. | |
| 6,007,614 A | 12/1999 | Billmers et al. | |
| 6,528,642 B1 | 3/2003 | Duval et al. | |
| 6,562,961 B1 | 5/2003 | Seeger et al. | |
| 7,919,111 B2 | 4/2011 | Chudzik et al. | |
| 2002/0058763 A1 | 5/2002 | Duval | |
| 2002/0123624 A1 | 9/2002 | Qiao et al. | |
| 2003/0215649 A1 | 11/2003 | Jelle | |
| 2004/0037886 A1 | 2/2004 | Hsu | |
| 2004/0208985 A1 | 10/2004 | Rowan et al. | |
| 2005/0019371 A1 | 1/2005 | Anderson et al. | |
| 2005/0255142 A1 | 11/2005 | Chudzik et al. | |
| 2006/0249705 A1 | 11/2006 | Wang et al. | |
| 2007/0065481 A1 | 3/2007 | Chudzik et al. | |
| 2007/0087025 A1 | 4/2007 | Fitzhugh et al. | |
| 2007/0218102 A1 | 9/2007 | Chudzik et al. | |
| 2007/0224247 A1 | 9/2007 | Chudzik et al. | |
| 2007/0260054 A1 | 11/2007 | Chudzik | |
| 2008/0038354 A1* | 2/2008 | Slager et al. | 424/487 |
| 2008/0039931 A1* | 2/2008 | Jelle et al. | 623/1.18 |
| 2010/0093662 A1 | 4/2010 | Defaye et al. | |
| 2010/0099861 A1 | 4/2010 | Okamoto et al. | |
| 2010/0303879 A1 | 12/2010 | Kurdyumov et al. | |
| 2010/0316687 A1 | 12/2010 | Swan et al. | |
| 2011/0076314 A1 | 3/2011 | Kurdyumov | |
| 2011/0076337 A1 | 3/2011 | Slager et al. | |
| 2011/0159067 A1 | 6/2011 | Rolfes Meyering | |
| 2011/0159101 A1 | 6/2011 | Kurdyumov et al. | |

FOREIGN PATENT DOCUMENTS

| | | |
|---|---|---|
| EP | 0 405 917 | 1/1991 |
| JP | 2001/321094 | 3/2001 |
| WO | 02/094224 | 11/2002 |

OTHER PUBLICATIONS

Péan, et al. (1999) *Why Does PEG 400 Co-Encapsulation Improve NGF Stability and Release from PLGA Biodegradable Microspheres?* Pharmaceutical Research 16: 1294-1299.

Varela, et al., (2005) *Evaluation of biochemical analytes in vitreous humor collected after death in West Indian manatees*, JAVMA 226: 88-92.

Chen, et al., (1995) *Enzymatic and chemoenzymatic approaches to synthesis of sugar-based polymer and hydrogels*, Carbohydrate Polymers 28: 15-21.

van Veen, et al. (2005) *The Effect of powder blend and tablet structure on drug release mechanisms of hydrophobic starch acetate matrix tablets*, European Journal of Pharmaceutics and Biopharmaceutics 61: 149-157.

Tarvainen, et al. (2004) *Aqueous starch acetate dispersion as a novel coating material for controlled release products*, Journal of Controlled Release 96: 179-191.

Magdassi, et al. (2001) *Interfacial Properties of Hydrophobically Modified Biomolecules: Fundamental Aspects and Applications*, J. Dispersion Science and Technology 22: 313-322.

Na, et al. (2003) *Self-assembled nanoparticles of hydrophobically-modified polysaccharide bearing vitamin H as a targeted anti-cancer drug delivery system*, European Journal of Pharmaceutical Sciences 18: 165-173.

Uekama, K. (2004) *Pharmaceutical Application of Cyclodextrins as Multi-functional Drug Carriers*, Yakugaku Zasshi 124: 909-935.

Kaur, et al. (2004) *Role of Cyclodextrins in Ophthalmics*, Current Drug Delivery 1: 351-360.

\* cited by examiner

*Primary Examiner* — Blessing Fubara
(74) *Attorney, Agent, or Firm* — Kagan Binder, PLLC

(57) ABSTRACT

Hydrophobic α(1→4)glucopyranose polymers useful for the preparation of implantable or injectable medical articles are described. The hydrophobic α(1→4)glucopyranose polymer includes pendent groups having hydrocarbon groups and terminal amine or hydroxyl groups. Biodegradable matrices can be formed from these polymers, and the matrices can be used for the preparation of implantable and injectable medical devices wherein the matrix is capable of degrading in vivo. Matrices including and capable of releasing a bioactive agent in vivo are also described.

22 Claims, No Drawings

HYDROPHOBIC POLYSACCHARIDES WITH PENDENT GROUPS HAVING TERMINAL REACTIVE FUNCTIONALITIES AND MEDICAL USES THEREOF

PRIORITY CLAIM

This application claims the benefit of U.S. Provisional Patent Application Ser. No. 61/291,172, filed Dec. 30, 2009, entitled HYDROPHOBIC POLYSACCHARIDES WITH PENDENT GROUPS HAVING TERMINAL REACTIVE FUNCTIONALITIES, the disclosure of which is incorporated herein by reference.

TECHNICAL FIELD

The present invention relates to hydrophobic derivatives of polysaccharides, and articles including these derivatives for use within the body.

BACKGROUND

Biodegradable polymers have been used to prepare biodegradable polymeric matrices that can be associated with, or formed into, implantable medical devices. For example, biodegradable polymers can be used to make a thin coating on a medical device surface. Such coatings can enhance the function of the device. Biodegradable polymers having thermoplastic properties can even be molded or formed into a shape to provide an implantable device having a structural property useful for treating a medical condition at the site of implantation. In theory, the polymeric matrix becomes completely degraded in the body. This can be advantageous for various medical applications, for example, such as to eliminate the requirement for explantation of the implanted article.

Implantable articles having biodegradable polymeric matrices can also be used to modulate the delivery of drugs to a patient at the site of implantation. Drug-releasing biodegradable matrices can be in the form of a coating on a device, or in the form of an implantable or injectable article that is formed primarily of the biodegradable polymer. Drug contained within the biodegradable matrix can be released or eluted from the matrix after the article has been introduced into the body.

Although there is a considerable amount of information regarding the use of biodegradable polymers for implantable medical devices, this field remains very technically challenging from a number of standpoints. For example, although biodegradable polymers should have properties suitable for the formation of a polymeric matrix in a desired form (such as a coating or a microparticle) it is often difficult to prepare such forms using conventional biodegradable polymers.

Also, the biodegradable polymeric matrix should be biocompatible, as well as the products that it degrades into. The polymeric matrix should not elicit a body response that would adversely affect its intended function, such as a negative tissue response (e.g., a prolonged inflammatory response) at the site of implantation. Poly(lactide) and poly(glycolide) have considerable use as biodegradable polymers for implantable devices, but there are concerns regarding the amount of acidic degradation products generated upon their hydrolysis.

Another challenge relates to the actual biodegradability of the matrix that is implanted or injected in the body. Although many biodegradable polymers exhibit biodegradability in in vitro systems, they may not degrade in matrix form after the matrix has been introduced into the body. In other words, the particular physical form of the matrix may obstruct chemical or enzymatic activity required for degradation of the polymer which is otherwise seen when the polymer is free in solution and subjected to these degrading chemical or enzymatic activities. Accordingly, a lack of biodegradability of the polymeric matrix can diminish or negate the intended function of the device.

SUMMARY OF THE INVENTION

Generally, the present invention relates to hydrophobic derivatives of natural biodegradable polysaccharides with chemistries that make the polymer more amenable for use in association with, or as a part of, an implantable or injectable medical device. The invention also relates to polymeric matrices formed from these polymers, articles including or associated with these polymeric matrices, and methods for using these matrices, such as for the treatment of a medical condition.

In one aspect, the invention provides a hydrophobic $\alpha(1\rightarrow4)$glucopyranose polymer comprising one or more pendent group(s) having a hydrocarbon segment and a hydroxyl or amine group at a terminus of the pendent group. Optionally, and in addition to the pendent group having a hydrocarbon segment and a terminal hydroxyl or amine group, the polymer can include one or more additional pendent group(s) comprising a hydrocarbon segment, but without a hydroxyl or amine group. The hydrocarbon segments can represent the hydrophobic portion of the polymer and can provide hydrophobic properties.

The presence of a hydroxyl or amine group at a terminus of the pendent group improves use of the hydrophobic $\alpha(1\rightarrow4)$ glucopyranose polymer in one or more ways. It has been found, in certain cases, that the hydrophobicity of a hydrophobic $\alpha(1\rightarrow4)$glucopyranose polymer makes it difficult to form a matrix that is stably associated with another material surface. For example, it can be difficult to keep a coated hydrophobic $\alpha(1\rightarrow4)$glucopyranose polymer stably associated with certain surfaces of an implantable device.

The presence of an amine or hydroxyl groups at a terminus of a pendent group can overcome certain challenges with substrate association by allowing bonding between the polymer and the device, or other material, via the amine or hydroxyl group. For example, covalent or non-covalent (e.g., ionic) bonding can provide improved attachment to the device surface. The surface on which the polymer is applied can be amine- or hydroxyl-reactive, thereby forming a covalent link between the hydrophobic $\alpha(1\rightarrow4)$glucopyranose polymer and the substrate. As such, polymeric matrices, such as in the form of coatings, can have better physical properties. For example, a coating formed using a hydrophobic $\alpha(1\rightarrow4)$ glucopyranose polymers of the invention can have improved properties with regard to one or more of coating thickness, the ability to stay laminated to the surface (as opposed to being delaminated), and compliance. In turn, this can improve the use of a coated implantable medical device in vivo, as the coating is less likely to fail and render the device non-functional. A coating resistant to delamination from the surface provides advantages for use within the body.

The particular hydroxyl and/or amine chemistry provides other advantages for use of the hydrophobic $\alpha(1\rightarrow4)$glucopyranose polymer. For example, the pendent group modification can space a terminal amine or hydroxyl group away from the polymer backbone, with the spacing is provided by at least the hydrocarbon segment. The spacing can increase the likelihood that the amine or hydroxyl group at a terminus of the pendent group will react with a hydroxyl- or amine-reactive target. On the other hand, natural (unreacted) hydroxyl groups may be subjected to steric hindrance from the polymer backbone, or steric hindrance from nearby pendent groups containing a hydrocarbon segment. In addition, for pendent groups that include a terminal hydroxyl group, pendent group formation can result in a re-formation of primary hydroxyl groups, which are more reactive than the natural secondary hydroxyl groups. Also, hydrophilic terminal amine or hydroxyl group is spaced away from the hydrophilic $\alpha(1\rightarrow 4)$ glucopyranose polymer backbone by the hydrophobic hydrocarbon segment. This may allow the polymer to become aligned on a surface, and result in a polymeric matrix (e.g., a coating) with more desirable and consistent properties.

The terminal amine or hydroxyl groups can also be used to provide crosslinking between polymers. For example, an amine- or hydroxyl-reactive component can be added to the composition that includes the polymer. The addition of such a component can cause crosslinking of the hydrophobic $\alpha(1\rightarrow 4)$glucopyranose polymers, or bonding to one or more other optional components in the polymer-containing composition.

As a general matter, biodegradable polymeric matrices can be formed from these hydrophobic $\alpha(1\rightarrow 4)$glucopyranose polymers having pendent groups with hydroxyl or amine-terminal groups. The matrices can be in various forms. These forms include a coated layer on a device surface, a three-dimensional implant, or microparticles. In some cases, the matrices can be associated with an implantable article, which can be fabricated from a material that is different than the biodegradable polymers of the invention.

Therefore, in other aspects, the invention provides an implantable or injectable biomedical article, the article comprising a polymeric matrix comprising a hydrophobic $\alpha(1\rightarrow 4)$glucopyranose polymer having pendent groups with a hydroxyl or amine group at a pendent group terminus. In some cases the hydroxyl or amine group is covalently reacted with a second material of the implantable or injectable biomedical article. The second material can be any amine or hydroxyl-reactive material, such as another polymer, a crosslinking compound, or a non-polymeric material. The second material can be associated with, or form, a device upon which the polymer is coated. As another example, the second material can be present within the matrix that is formed from the hydrophobic $\alpha(1\rightarrow 4)$glucopyranose polymer.

Articles formed from or associated with polymeric matrices including the hydrophobic $\alpha(1\rightarrow 4)$glucopyranose polymers can be introduced into the body. The matrices can be placed at a target location in a subject (i.e., in vivo). After a period of time, the polymeric matrix can degrade. Degradation can be caused by enzymatic degradation of the poly $\alpha(1\rightarrow 4)$glucopyranose portion.

The pendent groups can also include a hydrolytically-cleavable linker segment between the hydrocarbon segment and a monomeric unit of the poly-$\alpha(1\rightarrow 4)$glucopyranose portion. In some aspects, degradation can be promoted by hydrolytic cleavage of linker segments (e.g., linker segments having ester groups) between the hydrocarbon segments and the monomeric units of the polymer. Generally, hydrolytic cleavage of a group in the linker segment can cause separation of the hydrocarbon segment from the polysaccharide backbone. In some cases, hydrocarbon segments are cleaved and released from the matrix to body fluid or tissue where they can be metabolized. In other cases, the poly $\alpha(1\rightarrow 4)$glucopyranose portion is linked to a second material (e.g., a device surface) through a reacted amine or hydroxyl group. In these cases, hydrolytic cleavage can result in the hydrocarbon segment remaining attached to the second material. As a result, the poly $\alpha(1\rightarrow 4)$glucopyranose portion may become loosened from the surface.

Loss or separation of the hydrocarbon segment from the polysaccharide backbone can reduce the hydrophobicity of the matrix and promote non-enzymatic hydrolysis. Loss or separation of the hydrocarbon segment can also increase susceptibility of the $\alpha(1\rightarrow 4)$glucopyranose portion to enzymatic degradation by amylases.

The $\alpha(1\rightarrow 4)$glucopyranose polymer portion can be degraded into natural materials, which provide advantages for compatibility of implantable articles. Degradation of the $\alpha(1\rightarrow 4)$glucopyranose polymer portion can result in the release of, for example, naturally occurring monosaccharides, such as glucose, which is a common serum component.

In some aspects, the polymeric matrix formed from the hydrophobic $\alpha(1\rightarrow 4)$glucopyranose polymer is associated with an implantable or injectable medical article capable of releasing a bioactive agent in a subject. The hydrophobic $\alpha(1\rightarrow 4)$glucopyranose polymer can be associated with the device so that it modulates release of the bioactive agent. For example, in some aspects, bioactive agent is present within a matrix formed from the hydrophobic $\alpha(1\rightarrow 4)$glucopyranose polymer. Bioactive agent can be released from the matrix by elution out of the matrix, degradation of the matrix material, or both. Since the matrix can be completely degraded, the total amount of the bioactive agent contained in the matrix can be made available to the subject after a period of implantation. This allows the implants to be particularly useful for the treatment of medical conditions that require therapeutically effective amounts of a bioactive agent over a defined period of treatment.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the invention is directed to hydrophobic $\alpha(1\rightarrow 4)$glucopyranose polymers with pendent groups which include a hydrocarbon segment and a hydroxyl or amine group at a terminus of the pendent group. The invention is also directed to compositions including these hydrophobic $\alpha(1\rightarrow 4)$glucopyranose polymers, articles that are formed using these polymers, and methods for using articles formed from these polymers, such as drug delivery methods for the treatment of a medical condition.

An $\alpha(1\rightarrow 4)$glucopyranose polymer, which forms the poly-$\alpha(1\rightarrow 4)$glueopyranose portion of the hydrophobic $\alpha(1\rightarrow 4)$ glucopyranose polymer, includes repeating $\alpha$-D-glucopyranose ($Glc_p$) monomers having $\alpha(1\rightarrow 4)$ linkages. An unmodified portion (three monomeric units) of an $\alpha(1\rightarrow 4)$ glucopyranose polymer, is shown below:

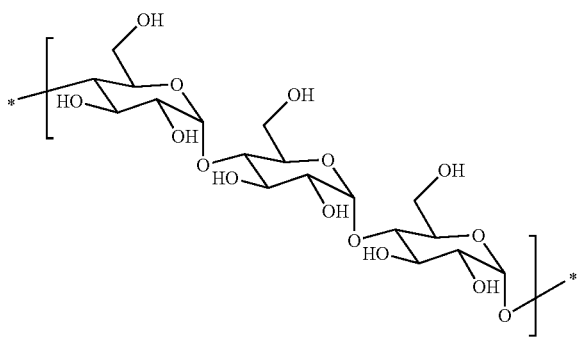

As starting material for the preparation of the hydrophobic α(1→4)glucopyranose polymer, one can use exemplary α(1→4)glucopyranose polymers, such as maltodextrin, amylose, cyclodextrin, and polyalditol (polyalditol is available from GPC (Muscatine, Iowa) under the tradename Innovatol™ PD60, and has <1% reducing sugars). Cyclodextrins are low molecular weight cyclic α(1→4)glucopyranose polymers.

Maltodextrin is typically generated by hydrolyzing a starch slurry with a heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate X 100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights are commercially available.

As used herein, "amylose" or "amylose polymer" refers to a linear polymer having repeating glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about $1 \times 10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1 \times 10^7$ Da or greater.

Exemplary maltodextrin and amylose polymers have molecular weights ranging from about 500 Da to about 500,000 Da, about 1000 Da to about 300,000 Da, and about 5000 Da to about 100,000 Da.

Maltodextrin and amylose polymers of various molecular weights are commercially available from a number of different sources. For example, Glucidex™ 6 (ave. molecular weight ~95,000 Da) and Glucidex™ 2 (ave. molecular weight ~300,000 Da) are available from Roquette (France); and MALTRIN™ maltodextrins of various molecular weights, including molecular weights from about 12,000 Da to 15,000 Da are available from GPC (Muscatine, Iowa).

The decision of using amylose or maltodextrin of a particular size range may depend on factors such as the physical characteristics of the composition, the desired rate of degradation of the matrix formed from the polysaccharide, and the presence of other optional components in the matrix, such as bioactive agents.

Refinement of the molecular weight of a polymer preparation (such as the α(1→4)glucopyranose polymer starting material) can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 KDa to about 10 kDa.

The polymers as discussed herein can be described in terms of molecular weight. "Molecular weight," as used herein, more specifically refers to the "weight average molecular weight" or $M_w$, which is an absolute method of measuring molecular weight and is particularly useful for measuring the molecular weight of a polymer (preparation). Polymer preparations typically include polymers that individually have minor variations in molecular weight. In some cases, the polymers have a relatively higher molecular weight (e.g., versus smaller organic compounds) and such minor variations within the polymer preparation do not affect the overall properties of the polymer preparation (for example, the characteristics of an polymer preparation). The weight average molecular weight ($M_W$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all NM; (species) in a preparation. The $M_w$ can be measured using common techniques, such as light scattering or ultracentrifugation. Discussion of $M_w$, and other terms used to define the molecular weight of polymer preparations can be found in, for example, Allcock, H. R. and Lampe, F. W., *Contemporary Polymer Chemistry*; pg 271 (1990).

As a general matter, the hydrophobic α(1→4)glucopyranose polymer can be considered to have at least two main portions. The first portion is an α(1→4) glucopyranose polymeric backbone. The second portion is a group (or generally a plurality of groups) pendent from the α(1→4)glucopyranose polymeric backbone (also referred to herein as "pendent groups"). In many modes of practice, the pendent groups are added to the backbone of a natural α(1→4)glucopyranose polymer through a chemical derivatization process. The pendent group(s) includes a hydrocarbon-containing segment linked to the monomeric unit of the α(1→4)glucopyranose polymer and a terminal hydroxyl or amine group. The hydrophobic polymer that is formed as a result of derivation to add the pendent groups provides a polymer that can subsequently be used or reacted to form a polymeric matrix.

In some cases the hydrophobic α(1→4)glucopyranose polymer can include a second set of pendent groups that include a hydrocarbon segment but that do not include a terminal hydroxyl or amine group. In some aspects the hydrophobic α(1→4)glucopyranose polymer has more first pendent group than second pendent groups. In some aspects, the hydrophobic α(1→4)glucopyranose polymer has an equal number of first pendent groups and second pendent groups. In some aspects, the hydrophobic α(1→4)glucopyranose polymer has more second pendent group than first pendent groups.

Unless otherwise noted, and to facilitate discussion of the invention, a hydrophobic α(1→4)glucopyranose polymer having pendent groups including a hydrocarbon segment and a terminal hydroxyl or amine group will be referred to herein as a "hydrophobic α(1→4)glucopyranose polymer."

The hydrophobic α(1→4)glucopyranose polymer includes pendent groups that include at least one hydrocarbon segment comprising two or more carbon atoms. According to the discussion herein, and unless otherwise noted, "pendent groups" refer to those chemical groups added, generally via a synthetic process, to the glucopyranose ring of a monomeric unit of the α(1→4)glucopyranose polymer. Typically, the pendent groups are formed by reacting one or more hydroxyl groups of a glucopyranose ring with one or more compounds that provides the pendent group(s). For purposes of discussion, natural hydroxyl groups present on the 2, 3, and/or 6 positions of the glycopyranose ring of a monomeric unit that are not reacted to provide pendent groups will be referred to as "natural hydroxyl groups" or "unreacted hydroxyl groups" of the polysaccharide.

The level of derivatization of an α(1→4)glucopyranose polymer with pendent groups containing hydrocarbon segments is generally sufficient to provide a polysaccharide derivative that has hydrophobic properties. Therefore, in some aspects, the sum amount of the hydrocarbon segments (i.e., the hydrocarbon segments of all pendent groups that include hydrocarbon segments) constitutes the hydrophobic portion of the polymer. The hydrophobic α(1→4)glucopyranose polymer can include pendent groups having a hydrocarbon segment that is positioned between a terminal hydroxyl or amine group and the α(1→4)glucopyranose polymer backbone. In some aspects, the hydrophobic α(1→4)glucopyranose polymer can include first pendent groups comprising a hydrocarbon segment and a terminal hydroxyl or amine group, and second pendent groups comprising a hydrocarbon segment but without a terminal hydroxyl or amine group.

The pendent groups can also include a linker segment, which is positioned between a glucopyranose monomeric unit of the polymer and a hydrocarbon segment of a pendent group. The linker segment can include a group that can be hydrolytically cleavable, or hydrolytically stable. In some embodiments, most or all of the groups pendent from the hydrophobic α(1→4)glucopyranose polymer include linker segments with hydrolytically-cleavable groups. Examples of hydrolytically-cleavable groups include ester, thioester, carbonate ester, silyl ethers, and carbamate. In one preferred aspect, the hydrophobic α(1→4)glucopyranose polymer includes pendent groups with ester-containing linker segments. Use of ester-containing linker segments can facilitate degradation of a polymeric matrix made from the hydrophobic α(1→4)glucopyranose polymer.

Overall, the hydrophobic α(1→4)glucopyranose polymer displays hydrophobic properties. The polymer can be used to form a hydrophobic α(1→4)glucopyranose matrix, such as in the form of a degradable coating, an implantable drug delivery device, or microparticles.

The hydrocarbon segment in a pendent group can include two or more carbon atoms. The hydrocarbon segment can be saturated or unsaturated. The pendent group may also include a hydrocarbon segment that is partially saturated. Examples of hydrocarbon segments include linear and branched alkyl, alkenyl, alkynyl, as well as cyclic alkyl, cyclic alkenyl, aromatic hydrocarbon, and aralkyl groups The hydrocarbon segment can be a divalent hydrocarbon radical, such as a group of covalently bonded carbon atoms having the formula —$(CH_n)_m$—, wherein m is 2 or greater, and n is independently 2 or 1. A divalent hydrocarbon radical can be positioned between the terminal hydroxyl or amine group and, for example, a linker segment comprising a hydrolytically-cleavable group, such as an ester group. In some aspects, the hydrocarbon segment is a $C_2$-$C_{18}$-containing, a $C_2$-$C_{12}$-containing, a $C_4$-$C_8$-containing, or a $C_4$-$C_6$-containing linear, branched, or cyclic divalent hydrocarbon radical.

In forming the hydrophobic α(1→4)glucopyranose polymer, and in some modes of practice, one or more compounds which provides pendent group(s) that include a hydrocarbon segment and a terminal hydroxyl or amine group are reacted with an α(1→4)glucopyranose polymer. Typically, the one or more compounds are reacted with an α(1→4)glucopyranose polymer to provide a plurality of pendent groups, the pendent groups present at a desired level of substitution on the α(1→4)glucopyranose polymer.

In underivatized form, the glucopyranose units of an α(1→4)glucopyranose polymer includes monomeric units having a glucopyranose ring structure with primary hydroxyl groups (the number 6 carbon on the glycopyranose ring) and secondary hydroxyl groups (the number 2 and 3 carbons on the glycopyranose ring). In some modes of synthesis, primary and/or secondary hydroxyl groups can be reacted with one or more hydroxyl-reactive compound(s) to provide pendent groups that replace the primary and/or secondary hydroxyl group on the glucopyranose monomeric unit. Generally, the primary (number 6 carbon) hydroxyl group on a glucopyranose ring is more reactive than the secondary hydroxyl groups. Therefore, reaction with a limited quantity of reactive compound will form an α(1→4)glucopyranose polymer derivative with more primary hydroxyls than secondary hydroxyls modified with pendent groups. Reaction can also result in a portion of primary hydroxyls modified with pendent groups, but no secondary hydroxyls modified on the polysaccharide portion.

The amount of pendent groups provided by derivation of the hydroxyl groups of the polymer backbone can be described, in some cases, by a degree of substitution (DS). DS is defined as the average number of pendent groups linked to each monomeric unit of the hydrophobic α(1→4)glucopyranose polymer. As a general matter, since each monomeric unit in an α(1→4)glucopyranose polymer has three hydroxyls available for modification, DS values range from zero to three (full substitution). (For example, substitution of one hydroxyl group per two glucopyranose units of the polymer results in a DS of 0.5.) The hydrophobic α(1→4)glucopyranose polymer can, in some instances, be defined in terms of one or more of the following: DS of the polymer with pendent groups containing the hydrocarbon group and the hydroxyl or amine terminal group, or total DS, if the hydrophobic α(1→4)glucopyranose polymer is synthesized with one or more additional pendent groups that differ from the pendent groups containing the hydrocarbon group and hydroxyl or amine terminal group.

Also, depending on the total level of derivatization with pendent groups, the hydrophobic α(1→4)glucopyranose polymer can include (a) derivatized glucopyranose monomeric units and underivatized glucopyranose monomeric units (e.g., a polymer having a DS of less than 1.0) or (b) derivatized glucopyranose monomeric units and no underivatized glucopyranose monomeric units (e.g., a polymer having a DS of 1.0 or greater).

The type of hydrocarbon segment in the pendent group can also influence the hydrophobic properties of the polymer. Generally, if compounds having large hydrocarbon groups (e.g., longer alkyl groups) are used for the synthesis of the hydrophobic polysaccharide, a smaller amount of the compound may be needed for reaction with the α(1→4)glucopyranose polymer to provide hydrophobicity. In other words, as the chain length of the alkyl group increases, the amount of the compound needed to provide a hydrophobic polysaccharide can decrease. Compounds with shorter hydrocarbon segments may be reacted with an α(1→4)glucopyranose polymer to provide a higher DS, whereas compounds with longer hydrocarbon segments may be reacted with an α(1→4)glucopyranose polymer to provide a lower DS.

For example, if a compound having a hydrocarbon segment with an alkyl chain length of $C_x$ is used to prepare a hydrophobic polysaccharide with a DS of 1, a compound having a hydrocarbon segment with an alkyl chain length of $C_{(2x)}$ is reacted in an amount to provide a hydrophobic polysaccharide (with comparable hydrophobicity) with a DS of 0.5.

The degree of substitution can influence the hydrophobic character of the polysaccharide. In turn, polymeric matrices formed from hydrophobic α(1→4)glucopyranose polymers having a high weight ratio of the hydrophobic portion to the α(1→4)glucopyranose polymer portion (as exemplified by a high DS) are generally more hydrophobic and can be more resistant to degradation.

In an exemplary mode of synthesis, pendent groups having a hydrocarbon segment and a terminal hydroxyl group are formed by the reaction of an alkyl diol, such as 1,6 hexanediol, with maltodextrin. To promote the reaction, a compound such as 1,1'-carbonyl diimidazole (CDI) is added to the maltodextrin solution in an amount in the range of about 0.5 to about 9 mmol/gram of maltodextrin (6 mmol/gram is average). (D.S of about 0.1 to 1.5) 1,1'-Carbonyldiimidazole serves as a catalyst to convert a hydroxyl group on the glucopyranose ring to a carbonate ester group, following addition of the alkyl diol. Next, an alkyl diol, such as 1,6 hexanediol, is added to the maltodextrin solution. Generally, to avoid crosslinking of the maltodextrin, the 1,6 hexanediol is added in molar excess over the carbonyldiimidazole, for example at an 10:1 molar excess. The reaction takes place with heating (e.g., about 40-55° C.) overnight, and then is quenched with water. The solid (hydrophobic maltodextrin) can then be collected by vacuum filtration, washed with water, and further purified by dialysis.

For example, maltodextrin is reacted with 1,6 hexanediol at a weight ratio of approximately 1:14. Hexanediol has a molecular weight of approximately 118.18 Da (g/mol), and the hydrocarbon portion of this molecule constitutes approximately 71% by weight of the 1,6 hexanediol. In view of a theoretically complete reaction (i.e., 100% of the 1,6 hexanediol reacts to provide pendent groups on the maltodextrin) the weight ratio of the α(1→4)glucopyranose polymer (maltodextrin) to the hydrophobic portion (hexanoic hydrocarbon segment) is approximately 1:1.4 (DS of ~1).

The formed pendent group has a carbonate ester linkage, a $C_6$ hydrocarbon segment (divalent hexyl), and a hydroxyl group at the terminus of the pendent group.

In another exemplary mode of synthesis, pendent groups having a hydrocarbon segment and a terminal hydroxyl group are formed by the reaction of a cyclic ester, such as δ-valerolactone, with maltodextrin. To promote the reaction, a non-nucleophilic base, such as 1-methyl imidazole or N-methylmorpholine (NMM) is added to the maltodextrin solution in an amount in the range of about 0.5 to about 6 mmol/gram of maltodextrin (3 mmol/gram is average). Next, a cyclic ester, such as δ-valerolactone, is added to the maltodextrin solution. The valerolactone is added in one portion in a dilute solution to minimize opening of the valerolactone by a ring-opened pendent hydroxyl already on the backbone. The reaction proceeds quickly and can be quenched with slightly acidified water. The solid (hydrophobic maltodextrin) can then be collected by vacuum filtration, washed with water, and further purified by dialysis.

For example, maltodextrin is reacted with δ-valerolactone at a weight ratio of approximately 1.6:1. δ-Valerolactone has a molecular weight of approximately 100.116 Da (g/mol), and the hydrocarbon portion of this molecule constitutes approximately 56% by weight of the δ-valerolactone. In view of a theoretically complete reaction (i.e., 100% of the δ-valerolactone reacts to provide pendent groups on the maltodextrin) the weight ratio of the α(1→4)glucopyranose polymer (maltodextrin) to the hydrophobic portion (pentanoic hydrocarbon segment) is approximately 60:40.

The formed pendent group has an ester linkage, a $C_5$ hydrocarbon segment (divalent butyl), and a hydroxyl group at the terminus of the pendent group.

In other modes of synthesis, the maltodextrin is reacted with a compound that results in the formation of a branched structure in the pendent group. As such, each branch in a branched structure has a terminus, and therefore a single pendent group has two or more termini, with a hydroxyl group or an amine group at least at one of those termini. Examples of compounds that can be reacted with maltodextrin to provide a hydroxyl terminal branch and an alkyl terminal branch are 1,2 pentanediol, and 2-methyl-1,3-propanediol:

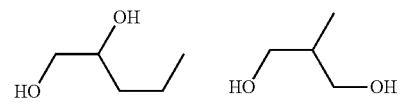

Examples of compounds that can be reacted with maltodextrin to provide a two hydroxyl terminal branches and one alkyl terminal branch are 2,2-bis(hydroxymethyl)butyric acid, and 2-methyl-1,3,5-pentanetriol:

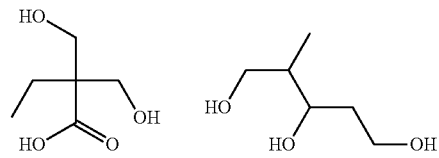

In another exemplary mode of synthesis, pendent groups having a hydrocarbon segment and a terminal amine group are formed by the reaction of an alkyl diamine, such as 1,6 hexanediamine, with maltodextrin. Again, a compound such as carbonyl-diimidazole can serve as a catalyst. Carbonyl-diimidazole can covert a hydroxyl group on the glucopyranose ring to a carbamate group, following addition of the alkyl diamine.

The alkyl diamine, such as 1,6 hexanediamine, can be added in molar excess over the carbonyl-diimidazole, for example at a 10:1 molar excess to avoid crosslinking of the polysaccharides. The reaction takes place with heating (e.g., about 55° C.) overnight, and then is quenched with water. The solid (hydrophobic maltodextrin) can then be collected by vacuum filtration, washed with water, and further purified by dialysis.

The formed pendent group has a carbamate linkage, a $C_6$ hydrocarbon segment (divalent hexyl), and an amine group at the terminus of the pendent group.

In another exemplary mode of synthesis, pendent groups having a hydrocarbon segment and a terminal amine group are formed by the reaction of a compound containing an amine-protected group with maltodextrin. The use of an amine-protecting group during synthesis can prevent reaction of a free amine group with other functional groups in the mixture. Examples of amine-protecting groups include t-butoxycarbonyl (BOC), fluorenylmethyl carbonyl (Fmoc), and trifluoroacetyl (TFA). Exemplary amine protected compounds that can be reacted with maltodextrin to provide a pendent groups with a terminal amine group include amine-protected (e.g., BOC) alanine, valine, and leucine. Exemplary amine protected compounds that can be reacted with maltodextrin to provide a pendent groups with terminal amine and hydroxyl groups include amine-protected (e.g., BOC) threonine and serine. Following derivatization of the maltodextrin, removal of these protecting groups can be performed using a strong acid (such as HCl) in an organic solvent (such as methanol).

In another mode of practice, N-protected cyclic amides such as N-Boc-ε-caprolactam can also be reacted with maltodextrin to provide pendent groups with an amine functional terminus. Reaction is generally carried out in the presence of a non-nucleophilic base, such as 1-methyl imidazole or N-methylmorpholine (NMM) to prevent ring-opening polymerization of the caprolactam.

Optionally, the hydrophobic α(1→4)glucopyranose polymer comprises two different pendent groups with one (e.g., a first pendent group) comprising the hydrocarbon segment and a hydroxyl or amine group at the terminus of the pendent group. Another pendent group (e.g., a second pendent group) is different than the first pendent group. In some aspects, the second pendent group includes a hydrocarbon segment, but does not include either a terminal hydroxyl or amine group.

Second pendent groups that include a hydrocarbon segment, but do not include either a terminal hydroxyl or amine group, can be formed by reacting a compound selected from fatty acids and derivatives thereof, such as fatty acid anhydrides and fatty acid halides, with maltodextrin. Exemplary fatty acids and anhydrides include acetic, propionic, butyric, isobutyric, valeric (pentanoic), caproic (hexanoic), enanthic (heptanoic), caprylic (octanoic), capric (decanoic), and lauric (dodecanoic) acids, anhydrides, and acid halides. A hydroxyl group of a polysaccharide can be reacted with a fatty acid, fatty acid anhydride, or fatty acid halides to bond the hydrocarbon group of the compound to the polysaccharide backbone via a formed ester group, which replaces the hydroxyl group on the polysaccharide. Use of these types of compounds provides the hydrocarbon segment at the terminus of the pendent group. Other compounds having hydroxyl-reactive groups and hydrocarbon groups (such as linear, branched, or cyclic hydrocarbon groups) can be reacted to provide pendent hydrocarbon-containing groups.

To provide a hydrophobic α(1→4)glucopyranose polymer with pendent first and second groups, first and second compounds can be reacted with an α(1→4)glucopyranose polymer. The first and second compounds can be reacted sequentially, or in combination (e.g., reacted as a mixture with an α(1→4)glucopyranose polymer). If a particular compound is reacted initially (either the first or second compound) then this compound will generally modify the primary hydroxyl groups of the α(1→4)glucopyranose polymer before the secondary hydroxyl groups. Depending on the amount of a first compound that is reacted, a portion of the primary hydroxyl groups, or all of the primary hydroxyl groups can be derivatized to first pendent groups.

In many aspects, the hydrophobic portion of the polymer includes the sum weight of all hydrocarbon segments. The relationship between the α(1→4)glucopyranose portion and the hydrophobic portion of the hydrophobic α(1→4)glucopyranose polymer can be described in various ways. For example, the relationship can be described as the ratio of the weight of the hydrophobic portion to the poly(α(1→4)glucopyranose portion.

In some aspects, in the hydrophobic α(1→4)glucopyranose polymer, the poly-α(1→4)glucopyranose portion and the hydrophobic portion are present at a weight ratio of about 2:1 (about 33 wt %) or greater, such as in the range of about 2:1 to about 1:-10, respectively. Derivatization with pendent groups that include a hydrocarbon group can also be described by DS. For example, in some aspects the DS on the hydrophobic α(1→4)glucopyranose polymer with pendent groups that include a hydrocarbon segment is in the range of about DS 0.1 to about DS 2.5, or more specifically in the range of about DS 0.5 to DS 2.

The relationship of the hydroxyl or amine terminal group in the polymer can be described in various ways, such as the ratio of the hydroxyl or amine functionality in moles to the weight of the α(1→4)glucopyranose polymer backbone, or the ratio of the hydroxyl or amine terminal group in moles to the weight of the hydrophobic portion.

In some aspects, the ratio of the hydroxyl or amine terminal group (mols) to the weight of the α(1→4)glucopyranose polymer backbone is in the range of about 0.5 mmol:1 gram to about 18 mmol:1 gram, and more specifically in the range of about 2 mmol: 1 gram to about 15 mmol:1 gram.

As used herein, the term "linker segment" is used to describe the chemistry between a hydrocarbon segment (in a pendent group) and the monomeric unit of the polysaccharide. As discussed, hydroxyl reactive groups can be used to form ester-containing linker segments. Other reactive chemistries associated with hydroxyl group derivatization on the polysaccharide can provide hydrolytically-cleavable groups, such as thioester, carbonate ester, silyl ether, and carbamate in the linker segment. Linker segment chemistries can be chosen to provide those experiencing faster rates of hydrolytic cleavage (e.g., ester, carbonate, silyl ether), or those experiencing slower rates of hydrolytic cleavage (e.g., carbamate).

The hydrophobic α(1→4)glucopyranose polymer can be prepared with pendent groups having linker segments with the same linker chemistry (e.g., all of the pendent groups have an ester-containing linker segment). Alternatively, the pendent groups can have different linker chemistries (e.g., a combination of pendent groups with ester and ester carbonate groups).

In some aspects, the hydrophobic α(1→4)glucopyranose polymer can include monomeric units of formula I:

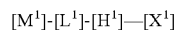     Formula I wherein $M^1$ is a monomeric unit of the poly-α(1→4)glucopyranose portion, $X^1$ is a hydroxyl or amine functionality, $H^1$ is a hydrocarbon segment, and $L^1$ is a linking group. In some aspects, the hydrophobic α(1→4)glucopyranose polymer includes a hydrocarbon segment ($H^1$) selected from a C2-C8 hydrocarbon segment for every one monomeric unit ($M^1$).

Optionally, the hydrophobic α(1→4)glucopyranose polymer can include monomeric units of formula I (as defined above) and formula II:

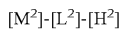  Formula II wherein $M^2$ is a monomeric unit of the poly-α(1→4)glucopyranose portion, $H^2$ is a hydrocarbon segment, and $L^2$ is a linking group.

In some aspects, in formula I: $[M^1]$-$[L^1]$-$[H^1]$—$[X^1]$, the linkage between $[M^1]$-$[L^1]$ is derived from a primary hydroxyl group position of $[M^1]$.

More than one (and up to three) pendent groups can be formed on a monomeric unit. Generally, the presence of a pendent group introduced on a monomeric unit means that the monomeric unit has been "modified." The hydrophobic α(1→4)glueopyranose polymer can also include unmodified monomeric units.

The pendent group(s) (e.g., -$[L^1]$-$[H^1]$—$[X^1]$ from formula I and/or -$[L^2]$-$[H^2]$ from formula II) can be formed from a primary hydroxyl group on the monomeric unit (i.e., the hydroxyl group off the #6 carbon on the glucopyranose ring), from a secondary hydroxyl group on the monomeric unit (i.e., one or both of the hydroxyl group(s) of the #2 and/or #3 carbon(s) on the glucopyranose ring), or from both primary and secondary hydroxyl groups on the monomeric unit.

In some aspects, one or more of $L^1$ and/or $L^2$ in Formula I and II, respectively, is a linking group independently selected from an ester or an ester carbonate group.

In some aspects, the hydrophobic poly-α(1→4)glucopyranose polymer comprises a monomeric unit according to Formula III:

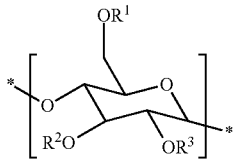

wherein one or more of $R^1$, $R^2$, and/or $R^3$ is $R^4R^5R^6$, wherein $R^4$ is —C(O)—,
—C(O)O—, or —C(O)N—, $R^5$ is a divalent linear, branched, or cyclic alkyl radical, and $R^6$ is —OH or —NH$_2$. For any of $R^1$, $R^2$, or $R^3$ that is not $R^4R^5R^6$ then $R^1$, $R^2$, and/or $R^3$ can be —H, or $R^{10}R^{11}$ as defined below. In some aspects, $R^1$ is $R^4R^5R^6$ as defined above, and $R^2$ and $R^3$ are —H.

In some aspects $R^5$ is a $C_2$-$C_{18}$ divalent linear, branched, or cyclic alkyl radical, a $C_2$-$C_{12}$ divalent linear, branched, or cyclic alkyl radical, or a $C_4$-$C_8$ divalent linear, branched, or cyclic alkyl radical. In exemplary embodiments, $R^5$ is a $C_4$, $C_5$, or $C_6$ divalent linear or branched alkyl radical.

In some aspects $R^4$ is —C(O)—.

Optionally, and in some aspects, in addition to a monomeric unit according to Formula III, the hydrophobic poly-α (1→4)glucopyranose polymer can also include a monomeric unit according to Formula IV:

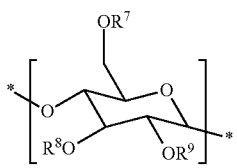

wherein one or more of $R^7$, $R^8$, and/or $R^9$ is $R^{10}R^{11}$, wherein $R^{10}$ is —C(O)—,
—C(O)O—, or —C(O)N—, and $R^{11}$ is a monovalent linear, branched, or cyclic alkyl radical.

For $R^7$, $R^8$, or $R^9$ that is not $R^{10}R^{11}$ then $R^7$, $R^8$, and/or $R^9$ can be —H.

In some aspects $R^{10}$ is a $C_2$-$C_{18}$ monovalent linear, branched, or cyclic alkyl radical, a $C_2$-$C_{12}$ monovalent linear, branched, or cyclic alkyl radical, or a $C_4$-$C_8$ monovalent linear, branched, or cyclic alkyl radical. In exemplary embodiments, $R^{10}$ is a $C_4$, $C_5$, or $C_6$ monovalent linear or branched alkyl radical.

Optionally, and in some aspects, in addition to a monomeric unit according to Formula III, the hydrophobic poly-α (1→4)glucopyranose polymer can also include a monomeric unit according to Formula V:

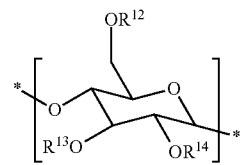

wherein one or more of $R^{12}$, $R^{13}$, and/or $R^{14}$ is according to formula VI:

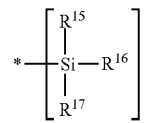

wherein one or more of $R^{15}$, $R^{16}$, and/or $R^{17}$ are independently selected from and include $C_1$-$C_{18}$ hydrocarbon groups, and preferably —CH$_3$, or —CH$_2$CH$_3$, with the proviso that the total number of carbon atoms in $R^{15}$, $R^{16}$, and $R^{17}$ is at least three. Hydrophobic α(1→4)glucopyranose polymer containing these silyl ether linking groups are also described in commonly assigned and copending U.S. application Ser. No. 12/894,929, filed Sep. 30, 2010; Kurdyumov).

The hydrophobic α(1→4)glucopyranose polymer can be soluble in a single solvent or combination of solvents. Exemplary solvents or dispersant include, but are not limited to, alcohols (e.g., methanol, ethanol and isopropanol), alkanes (e.g., halogenated or unhalogenated alkanes such as hexane, methylene chloride and chloroform), ethers (e.g., tetrahydrofuran (THF)), ketones (e.g., acetone, methyl ethyl ketone, methyl isobutyl ketone), aromatic compounds (e.g., toluene and xylene), nitriles (e.g., acetonitrile), and ester (e.g., ethyl acetate and butyl acetate).

Within a particular solvent, the hydrophobic α(1→4)glucopyranose polymer may be determined to be soluble (having a solubility of at least 1 part agent per from 10 to 30 parts solvent), freely soluble (having a solubility of at least 1 part agent per from 1 to 10 parts solvent), or very soluble (having a solubility of greater than 1 part agent per 1 part solvent). These descriptive terms for solubility are standard terms used in the art (see, for example, *Remington: The Science and Practice of Pharmacy*, 20th ed. (2000), Lippincott Williams & Wilkins, Baltimore Md.).

The hydrophobic α(1→4)glucopyranose polymer has the properties of being insoluble in water. The term for insolubility is a standard term used in the art, and meaning 1 part solute per 10,000 parts or greater.

In some aspects, a hydrophobic α(1→4)glucopyranose polymer having a molecular weight within a predetermined size range is used. The molecular weight of the hydrophobic α(1→4)glucopyranose polymer can be described in terms of the starting molecular weight of the α(1→4)glucopyranose polymer, or the molecular weight of the fully derivatized polymer (i.e., including the pendent groups).

The addition of pendent groups including the hydrocarbon group and the acid-terminal functionality will generally cause a measurable increase in molecular weight of the poly α(1→4)glucopyranose polymer, from its underivatized, starting molecular weight. The amount increase in molecular weight can depend on one or more factors, the level of derivatization, and the chemical nature of the pendent groups.

In one aspect, the hydrophobic α(1→4)glucopyranose polymer has a molecular weight in the range of about 5 kDa to about 5000 kDa, and in more specific aspects a molecular weight in the range of about 25 kDa to about 1000 kDa.

The hydrophobic α(1→4)glucopyranose polymer can be present in a liquid composition including a solvent suitable to dissolve the polymer ("a polymer solvent"). Examples of preferred solvents that can be used to prepare a composition include halogenated alkanes such as methylene chloride and chloroform. Other solvents, including aromatic compounds such as toluene and xylene, ethers such as tetrahydrofuran, and amides such as dimethylformamide (DMF), can be used to dissolve the polymer. Combinations of one or more of these or other solvents can also be used.

Compositions including dissolved hydrophobic α(1→4) glucopyranose polymer in a solvent, or combination of solvents, can be used for the preparation of coatings, casting films, microparticles, or the preparation of implantable filaments.

In some aspects the composition includes a compound that is reactive with the hydroxyl or amine groups. For example, the compound can be a crosslinker that includes two or more amine- or hydroxyl-reactive groups. Examples include dialdehyde, diacrylate, and dianhydride crosslinking compounds. The crosslinking compound is preferably at least partially soluble in the solvent system that is used to dissolve the dissolved hydrophobic α(1→4)glucopyranose polymer. A crosslinking compound can be used for the preparation of a hydrophobic gel. Alternatively, a method of making a polymeric matrix from the hydrophobic α(1→4)glucopyranose polymer may include a step of using a compound that is reactive with the hydroxyl or amine groups. For example, in a coating process, a compound that is reactive with hydroxyl or amine groups may be applied to a surface in a step separate from a step of applying the hydrophobic α(1→4)glucopyranose polymer.

A composition including the hydrophobic α(1→4)glucopyranose polymer can also be provided in the form of an emulsion. For example, the hydrophobic α(1→4)glucopyranose polymer can be present in either an oil-in-water-type of emulsion, or a water-in-oil-type of emulsion. The presence of the terminal amine or hydroxyl groups in the polymer may enhance the ability of the hydrophobic α(1→4)glucopyranose polymer to assemble into emulsion particulates. In other words, the terminal amine or hydroxyl groups can reduce the overall hydrophobicity of the polymer and facilitate particle formation in an emulsion.

An oil-in-water-type of emulsion can include the hydrophobic α(1→4)glucopyranose polymer present in the dispersed phase. An oil-in-water-type of emulsion can be prepared by dissolving the polymer in a polymer solvent such as dichloromethane, chloroform, or another solvent that is immiscible with water. The solvated polymer can be added to an excess amount of continuous phase liquid, such as water or a water-based liquid. The continuous phase liquid can include one or more additional components that can stabilize the emulsion, promote the formation of particular discontinuous phase structures.

To form a water-in-oil-type of emulsion, water or a water-based liquid can be dispersed in a continuous phase liquid such as dichloromethane or chloroform having the solubilized hydrophobic α(1→4)glueopyranose polymer. After the discontinuous phase and continuous phase liquids are mixed the composition can be agitated, such as in a homogenizer, to promote emulsion formation.

The emulsion can also include an emulsion stabilizer. In some aspects, the emulsion stabilizer comprises a halogenated arylboronic acid as described in commonly assigned U.S. Application Ser. No. 61/247,408, filed Sep. 30, 2009, and entitled "EMULSIONS CONTAINING ARYLBORONIC ACIDS" (Slager et al).

The stability of these emulsions may facilitate the preparation of articles formed from these matrices as the emulsion of hydrophobic α(1→4)glucopyranose in the organic phase with an immiscible aqueous phase does not separate in the composition during use.

The hydrophobic α(1→4)glueopyranose polymer can be used to form articles that are wholly or partially degradable. A partially degradable article can be an article that has a biostable portion, such as a biostable body member, and a biodegradable portion, such as a biodegradable coating.

The polymeric matrices formed from the hydrophobic α(1→4)glucopyranose polymers can be used in many medical applications. These include drug delivery medical applications, as well as applications where drug delivery is not required. The applications can involve short term or long-term treatment of various conditions.

In some aspects, the hydrophobic α(1→4)glucopyranose polymer is used to form a body member, or a portion of a body member, of an implantable medical article. In these aspects, a degradable body member, or portion thereof, can provide mechanical properties at the implantation site and can maintain these mechanical properties until they are no longer needed. After a period of time has elapsed, the body member is degraded to an extent that the mechanical properties are no longer provided, and the degraded components of the article are processed by the body.

In some embodiments, the body member of the medical article slowly degrades and transfers stress at the appropriate rate to surrounding tissues as these tissues heal and can accommodate the stress once borne by the body member of the medical article. The medical article can optionally include a coating or a bioactive agent to provide one or more additional functional features; however, these are not required in order for the article to be of use at the treatment site.

The article can also comprise filaments and fibers, such as microfibers and/or nanofibers that are formed from the hydrophobic α(1→4)glucopyranose polymer. The filaments or fibers can be included in or associated with various articles including implantable medical articles. The filaments or fibers may be prepared with a bioactive agent to provide one or more additional functional features.

To illustrate one method of preparing the implantable medical article, a composition is prepared by combining bioactive agent and the hydrophobic α(1→4)glucopyranose polymer in solid form. The bioactive agent and the hydrophobic derivative are placed in a vessel and heated together, which melts the hydrophobic α(1→4)glucopyranose polymer. The composition is then mixed to blend the bioactive agent into the melted hydrophobic derivative. The composition can then be shaped into a desired form. An exemplary process is described in commonly assigned U.S. Patent Application Publication No. 2007/0224247 (Chudzik et al.). The composition may be treated during or after article formation to react the hydroxyl or amine groups in the pendent groups of the hydrophobic α(1→4)glucopyranose polymer.

In another aspect of the invention, the hydrophobic α(1→4)glucopyranose polymer is used to form a coated layer on a surface of a medical article. The hydrophobic α(1→4) glucopyranose polymer can be present in one or more coated layers on all or a portion of the surface of the device. A "coating" as used herein can include one or more "coated layers", each coated layer including one or more coating materials. In some cases, the coating can be formed of a single layer of material that includes the hydrophobic α(1→4)glucopyranose polymer. In other cases, the coating includes more than one coated layer, at least one of the coated layers including the hydrophobic α(1→4)glucopyranose polymer. If more than one layer is present in the coating, the layers can be composed of the same or different materials.

For the formation of a coating, a composition containing the hydrophobic α(1→4)glucopyranose polymer in a solvent system can be applied to the device surface, and then the solvent is removed from the applied composition. The terminal amine or hydroxyl group of the pendent group can undergo bonding to improve association of the polymer with the device surface and provide better properties to the coating. In some cases the bonding is covalent. As such, the terminal amine or hydroxyl group will become "reacted" to form a different chemical species. In some cases the device surface comprises an amine reactive group selected from isothiocyanate, NHS ester, epoxide, anhydrides, and the like. The reactive group can be provided by the device material or by an intermediate coated layer on the device, such as an amine-reactive polymer layer.

In some aspects the hydrophobic α(1→4)glucopyranose polymer is used in a base coat (e.g., tie layer) on the surface of a device. For example, a coating can be formed that includes a base coat including the hydrophobic α(1→4)glucopyranose polymer in contact with a the material of the device, and one or more other polymeric coated layers on top of the base coat. The hydroxyl or amine group of the hydrophobic α(1→4) glucopyranose polymer can be directly or indirectly bonded (e.g., through covalent or ionic bonding) to material of the device surface.

After the tie layer is formed, a composition containing a polymer and a bioactive agent can be applied to the base coat. The polymeric composition can include one or more polymeric components, which can be different than the hydrophobic α(1→4)glucopyranose polymer with the amine or hydroxyl group in the pendent group. For example, the polymeric composition can include a hydrophobic α(1→4)glucopyranose polymer without an amine or hydroxyl group in the pendent groups. In some cases, the one or more polymer(s) are able to blend into the base coat to a certain extent. This can provide a more durable and/or cohesive coating because the materials of the bioactive agent-releasing layer become partially mixed with the tie layer.

A coating composition (with or without bioactive agent) can be applied to a medical device using standard techniques to cover the entire surface of the device, or a portion of the device surface. If more than one coated layer is applied to a surface, it is typically applied successively. For example, a coated layer can be formed by, for example, dipping, spraying, bushing, or swabbing a coating composition including the hydrophobic α(1→4)glucopyranose polymer on the article to form a layer, and then removing the solvent from the applied composition to form the coated layer. The process can be repeated to provide a coating having multiple coated layers, wherein at least one layer includes the hydrophobic α(1→4)glucopyranose polymer. The compositions of the present invention are also suitable for use in a spray coating processes.

An exemplary spray coating process and apparatus that can be used for coating implantable medical articles using the compositions of the present invention is described in U.S. Pat. No. 7,192,484 (Chappa et al.)

A composition that includes the hydrophobic α(1→4)glucopyranose polymer can be spray coated directly onto the surface of a body member of a medical article, or can be spray coated onto a surface that includes one or more coated layers of material previously formed on the body member.

The following list of medical articles is provided to illustrate those that can that can be associated with a polymeric matrix made using the hydrophobic α(1→4)glucopyranose polymer. These types of articles are typically introduced temporarily or permanently into a mammal for the prophylaxis or treatment of a medical condition. For example, these articles can be introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects the polymeric matrix made using the hydrophobic α(1→4)glucopyranose polymer is associated with an ophthalmic article. For example, the matrix can be used as a coating on the surface of an ophthalmic article, or as a filament or drug delivery depot configured for placement at an external or internal site of the eye. In some aspects, the articles can be utilized to deliver a bioactive agent to an anterior segment of the eye (in front of the lens), and/or a posterior segment of the eye (behind the lens). Illustrative intraocular devices include, but are not limited to, those described in U.S. Pat. Nos. 6,719,750 B2 (Varner et al.) and 5,466,233 ("Tack for Intraocular Drug Delivery and Method for Inserting and Removing Same," Weiner et al.) Illustrative ophthalmic devices for subretinal application include, but are not limited to, those described in U.S. Patent Publication No. 2005/0143363 (de Juan et al.).

A polymeric matrix made using the hydrophobic $\alpha(1\rightarrow 4)$ glucopyranose polymer can be associated with a device formed of a non-biodegradable material. For example, a coating can be formed on a body member of a medical article that is partially or entirely fabricated from a plastic polymer. Plastic polymers include those formed of synthetic polymers, including oligomers, homopolymers, and copolymers resulting from either addition or condensation polymerizations. Examples of suitable addition polymers include, but are not limited to, acrylics (e.g, methyl acrylate) and vinyls (e.g., ethylene). Examples of condensation polymers include, but are not limited to, nylons (e.g., polycaprolactam) and also polyurethanes, polycarbonates, polyamides, polysulfones, poly(ethylene terephthalate), polydimethylsiloxanes, and polyetherketones.

The polymeric matrix can also be associated with an implantable medical article partially or entirely fabricated from a degradable polymer. The article can degrade in an aqueous environment, such as by simple hydrolysis, or can be enzymatically degraded. Examples of classes of synthetic polymers that can be used to form the structure of a degradable article include polyesters, polyamides, polyurethanes, polyorthoesters, polycaprolactone (PCL), polyiminocarbonates, aliphatic carbonates, polyphosphazenes, polyanhydrides, and copolymers thereof. As an example, the hydrophobic polysaccharide can provide a barrier coating to articles fabricated from polylactide or copolymers thereof. The coating can shield the article during a portion or all of a desired period of treatment. The coated article can still be fully degradable.

The polymeric matrix can also be associated with an implantable medical article that is partially or entirely fabricated from a metal. Although many devices or articles are constructed from substantially all metal materials, such as alloys, some may be constructed from both non-metal and metal materials, where at least a portion of the surface of the device is metal.

Commonly used metals include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

In some aspects a biodegradable coating is formed on the surface of an erodable implantable medical device formed from of a metal. For example, the biodegradable coating can be formed on a magnesium alloy stent that can be corroded following placement in a subject (see, for example, De Mario, C. et al. (2004) *J. Interv. Cardiol.*, 17(6):391-395, and Heublein, B., et al. (2003) *Heart;* 89:651-656). The erodable implantable medical device can be associated with a bioactive agent, if desired.

In aspects where the structure of the implantable medical article is fabricated from a material that is erodable or degradable, an in vivo lifetime of the article can be determined. Using the hydrophobic $\alpha(1\rightarrow 4)$glucopyranose polymer, a biodegradable coating can be formed the surface of these erodable or degradable articles to prolong their in vivo lifetime. For example, a coating formed from the hydrophobic $\alpha(1\rightarrow 4)$glucopyranose polymer can provide a hydrophobic biodegradable barrier which protects a degradable body member from degradation for a period of time. Upon degradation of the Wilier, the body member can quickly degrade. The in vivo lifetime is a period of time starting upon placement of the coated article at a target location, and ending when the coated article is completely degraded at the target location.

Other contemplated biomaterials include ceramics including, but not limited to, silicon nitride, silicon carbide, zirconia, and alumina, as well as glass, silica, and sapphire. Combinations of ceramics and metals can also be coated.

The biodegradable matrix can also be associated with an article having a porous structure, such as one formed of a fabric or that has fabric-like qualities. The porous structure can be formed from textiles, which include woven materials, knitted materials, and braided materials. Particularly useful textile materials are woven materials which can be formed using any suitable weave pattern known in the art.

The porous structure can be that of a graft, sheath, cover, patch, sleeve, wrap, casing, and the like, including many of the medical articles described herein. These types of articles can function as the medical article itself or be used in conjunction with another part of a medical article.

Other particular contemplated porous structures include grafts, particularly grafts having textured exterior portions. Examples of textured grafts include those that have velour-textured exteriors, with textured or smooth interiors. Grafts constructed from woven textile products are well known in the art and have been described in numerous documents, for example, U.S. Pat. No. 4,047,252; U.S. Pat. No. 5,178,630; U.S. Pat. No. 5,282,848; and U.S. Pat. No. 5,800,514.

Bioactive agents can also be associated with a coating or polymeric matrix formed from the polymer. For example, a coating can include a coated layer formed using the hydrophobic $\alpha(1\rightarrow 4)$glucopyranose polymer and bioactive agent. In some aspects, one or a combination of bioactive agents can be immobilized in a coated layer formed from the hydrophobic $\alpha(1\rightarrow 4)$glucopyranose polymer.

The term "bioactive agent," refers to an inorganic or organic molecule, which can be synthetic or natural, which causes a biological effect when administered in vivo to an animal, including but not limited to birds and mammals, including humans.

A partial list of bioactive agents is provided below. According to embodiments of the present invention, one may choose one or more of the bioactive agents to be included in an article or coating is associated with a matrix formed from the hydrophobic $\alpha(1\rightarrow 4)$glucopyranose polymer. A comprehensive listing of bioactive agents, in addition to information of the water solubility of the bioactive agents, can be found in *The Merck Index*, Thirteenth Edition, Merck & Co. (2001).

Articles and coatings prepared according to the invention can be used to release bioactive agents falling within one or more of the following bioactive agent classes. These classes include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

In some cases, the hydrophobic groups pendent from the α(1→4)glucopyranose backbone have properties of a bioactive agent. In these aspects, the hydrophobic group/bioactive agent can be hydrolyzed from the α(1→4)glucopyranose backbone and released from the matrix to provide a therapeutic effect in a subject. An example of a therapeutically useful compound having a hydrocarbon segment is butyric acid, which has been shown to elicit tumor cell differentiation and apoptosis, and is thought to be useful for the treatment of cancer and other blood diseases. Other illustrative compounds comprising hydrocarbon segments include valproic acid and retinoic acid. Retinoic acid is known to possess antiproliferative effects and is thought to be useful for treatment of proliferative vitreoretinopathy (PVR). Another illustrative compound that can be coupled to the polysaccharide backbone is a corticosteroid. An exemplary corticosteroid is triamcinolone.

Thin polymer free standing films can be prepared from a composition including the hydrophobic α(1→4)glucopyranose polymer. In some modes of practice, free standing films are prepared by spin casting the polymer on a glass substrate. The formed films can be floated on a water surface, and subsequently handled. The free-standing films can be shaped (such as by cutting) to provide a desired configuration.

In other aspects, the hydrophobic α(1→4)glucopyranose polymer is used to form an implantable or injectable medical article which also includes a bioactive agent. The implant may not have any distinct mechanical properties, such as would be apparent with an intravascular prosthesis, but rather provides a mechanism to deliver the bioactive agent to a particular portion of the body. The implant can have a defined structure and size that is appropriate for its use at a desired location in the body.

In some aspects the implantable or injectable medical article includes a matrix formed of the hydrophobic α(1→4) glucopyranose polymer which modulates the release of the bioactive agent from the article. For example, the matrix can be in the form of a barrier layer that the bioactive agent passes through before becoming available to the subject. Such a barrier layer can be in the form of a shell of polymeric material encapsulating a core comprising bioactive agent.

In other aspect, the implant is in the form of a filament, pellet, or the like, which contains a bioactive agent. The implant can be formed by a process such as solvent casting. A medical implant having a defined structure can be formed by any suitable process, including molding, extruding, shaping, cutting, casting, and the like.

In other aspects, the hydrophobic α(1→4)glucopyranose polymer is used to form a microparticle. The presence of the terminal amine or hydroxyl groups in the polymer can enhance the ability of the hydrophobic α(1→4)glucopyranose polymer to form microparticles, since the polymer is generally not excessively hydrophobic. In addition, use of the hydrophobic α(1→4)glucopyranose polymer allows for a broader range of solvents, and therefore provides benefits for the preparation and use of microparticles.

Microparticles including a hydrophobic α(1→4)glucopyranose polymer can be formed using an oil-in-water-type emulsion process, a water-in-oil-type emulsion process, or a spray drying process. Microparticles formed using a hydrophobic α(1→4)glucopyranose polymer microparticles can include a bioactive agent (such as a large biomolecule bioactive agent, like a protein). Processes such as solid (protein)/oil/water (single emulsion method), or water (aqueous protein solution)/oil/water (double emulsion method) can be used to prepare bioactive agent-containing microparticles.

In one mode of practice, hydrophobic α(1→4)glucopyranose polymer-based microparticles are formed using a water/oil/water (W/O/W) emulsion solvent extraction-evaporation method based on the techniques described in Péan, J.-P, et al. (1999) *Pharma. Res.*, 16:1294-1299. The microparticles formed using this method include a bioactive agent (Péan forms microparticles including nerve growth factor using human serum albumin as a carrier). However, a bioactive agent can be included or omitted from a process based on Péan using hydrophobic α(1→4)glucopyranose, as desired. In some modes of practice, if a bioactive agent is included it is used in an amount of up to about 10% (with respect to the weight of the hydrophobic α(1→4)glucopyranose polymer).

First, 0.15 mL of an aqueous phase buffered solution (e.g., 16 mM citrate buffer) and 5% human serum albumin (with respect to the amount of hydrophobic α(1→4)glucopyranose used) and containing 10 μg of a polypeptide-based bioactive agent is prepared. This is then added to, and emulsified in an organic solution (e.g., about 1.2-2.0 mL of an organic solvent such as dichloromethane, ethyl acetate, chloroform, etc., or mixtures thereof) containing 500 mg of hydrophobic α(1→4) glucopyranose. Emulsion is performed in a glass vial, suitable volume syringe (capped), or a thermoplastic tube (e.g., PTFE) with a lab mixer (e.g., a Silverson L4RT lab mixer with square hole head or Silverson, Model L4RT, 19 mm Tubular Head or IKA-T25 Ultra-Turrax, S 25 N-G, Coarse 8 mm diameter rotor-stater probe) for about 30-40 seconds. Mixing time can be varied based on the mixing speed and batch size or volume.

For the W/O/W (double emulsion method), after the primary emulsion is formed it is injected into a 100 mL solution of 2% PVA (in water) while homogenizing at 3000 rpm using the above-mentioned mixers for 30-40 sec. This is then poured into 600-700 mL of water, and stirred for 15 min at 300-500 rpm (using a stir-bar), followed by filtration and washing, etc.

For the solid/O/W (single emulsion method), the solid (protein) dispersed polymer solution is injected into a 100 mL solution of 2% PVA (in water) while homogenizing at 3000 rpm using the above-mentioned mixers for 30-40 sec. This is then poured into 600-700 mL of water, and stirred for 15 min at 300-500 rpm (using a stir-bar), followed by filtration and washing, etc.

Bioactive agents incorporated into the microparticles formed using these techniques can release a desired amount of the agent over a predetermined period of time. The bioactive agent can be released from the biodegradable microparticle upon degradation of the biodegradable microparticle in vivo.

Medical articles associated with a matrix formed from the hydrophobic α(1→4)glucopyranose polymer can be treated to sterilize one or more parts of the article, or the entire medical article. Sterilization can take place prior to using the medical article and/or, in some cases, during implantation of the medical article.

In some aspects, the invention provides a method for delivering a bioactive agent from coating or article associated with a matrix formed from the hydrophobic α(1→4)glucopyranose polymer. The bioactive agent can be present in a matrix formed from the hydrophobic α(1→4)glucopyranose polymer, or associated with a different portion of the article. For example, the matrix formed from the hydrophobic α(1→4) glucopyranose polymer may provide a barrier that the bioactive agent passes through, or the bioactive agent is releasable from a different polymeric layer that is also associated with the article.

In performing the method, the article is placed in a subject. Upon exposure to body fluid the bioactive agent may be released from a portion of the article. In some cases, depending on the arrangement of the matrix formed from the hydrophobic α(1→4)glucopyranose polymer in the article is subjected to degradation by non-enzymatic hydrolysis, enzymatic amylase activity, or both. A carbohydrase can promote the degradation of the polymeric matrix. Degradation may occur before, during, or after the release of the bioactive agent. Examples of carbohydrases that can specifically degrade natural biodegradable polysaccharide coatings include α-amylases, such as salivary and pancreatic α-amylases; disaccharidases, such as maltase, lactase and sucrase; trisaccharidases; and glucoamylase (amyloglucosidase).

Serum concentrations for amylase are estimated to be in the range of about 50-100 U per liter, and vitreal concentrations also fall within this range (Varela, R. A., and Bossart, G. D. (2005) *J Am Vet Med Assoc* 226:88-92).

In some aspects, the carbohydrase can be administered to a subject to increase the local concentration, for example in the serum or the tissue surrounding the implanted device, so that the carbohydrase may promote the degradation of the matrix. Exemplary routes for introducing a carbohydrase include local injection, intravenous (IV) routes, and the like. Alternatively, degradation can be promoted by indirectly increasing the concentration of a carbohydrase in the vicinity of the matrix, for example, by a dietary process, or by ingesting or administering a compound that increases the systemic levels of a carbohydrase.

In other cases, the carbohydrase can be provided on a portion of the article. For example the carbohydrase may be eluted from a portion of the article that does not include the matrix. In this aspect, as the carbohydrase is released it locally acts upon the coating to cause its degradation and promote the release of the bioactive agent.

EXAMPLE 1

As shown in the reaction scheme below, maltodextrin is dissolved into dimethylsulfoxide (DMSO) and stirred magnetically until fully dissolved at room temperature. N-Boc-Alanine is dissolved into an aliquot of DMSO, with an equivalent of N,N'-diisopropylcarbodiimide (CDI). This solution is premixed for 30 minutes and then added to the solution of maltodextrin. The catalyst, 4-(dimethylamino) pyridine (DMAP) is added to the final solution to enhance the esterification reaction. The coupling proceeds for 2 hours. The protected amino acid-modified polysaccharide can be purified using dialysis in deionized water in SpectraPor dialysis tubing. Lyophilization will yield the dried polymer. The t-butylcarboxyl (Boc) protecting group can be removed with acid hydrolysis using hydrochloric acid in methanol in an organic solvent. The final polymer can be dialyzed again to remove the cleaved protecting group and solvents, followed by lyophilization to achieve the final modified polysaccharide.

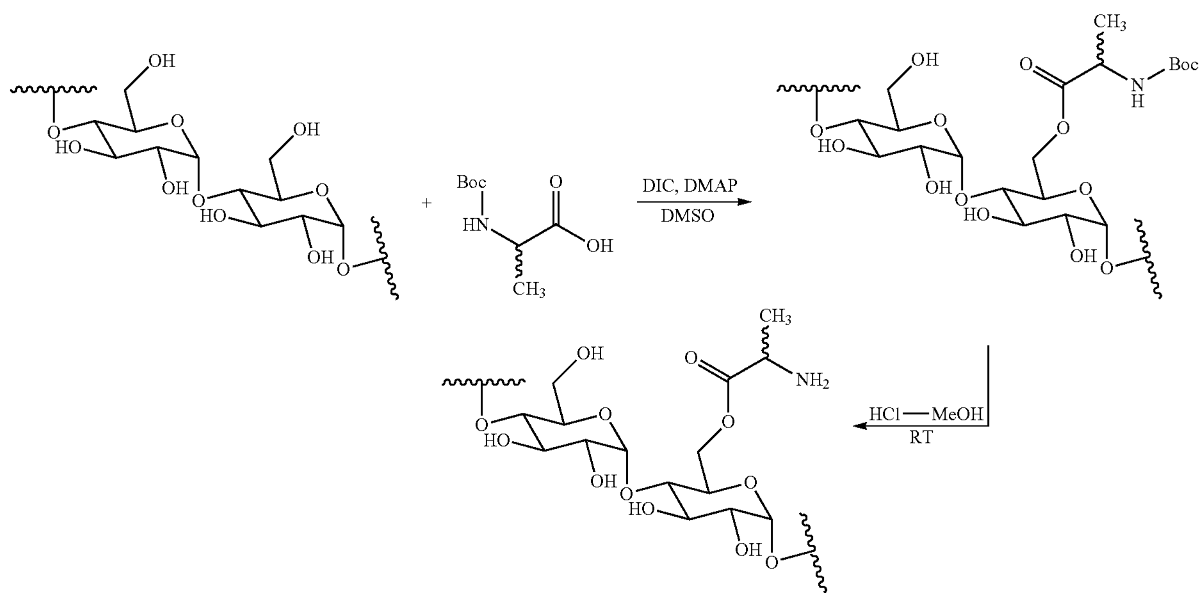

EXAMPLE 2

As shown in the reaction scheme below, maltodextrin is dissolved into dimethylsulfoxide (DMSO) and stirred magnetically until fully dissolved at room temperature. N-Boc-threonine is dissolved into an aliquot of DMSO, with an equivalent of N,N'-diisopropylcarbodiimide (CDI). This solution is premixed for 30 minutes and then added to the solution of maltodextrin. The catalyst, 4-(dimethylamino) pyridine (DMAP) is added to the final solution to enhance the esterification reaction. The coupling proceeds for 2 hours. The protected amino acid-modified polysaccharide can be purified using dialysis in deionized water in SpectraPor dialysis tubing. Lyophilization will yield the dried polymer. The t-butylcarboxyl (Boc) protecting group can be removed with acid hydrolysis using hydrochloric acid in methanol in an organic solvent. The final polymer can be dialyzed again to remove the cleaved protecting group and solvents, followed by lyophilization to achieve the final modified polysaccharide.

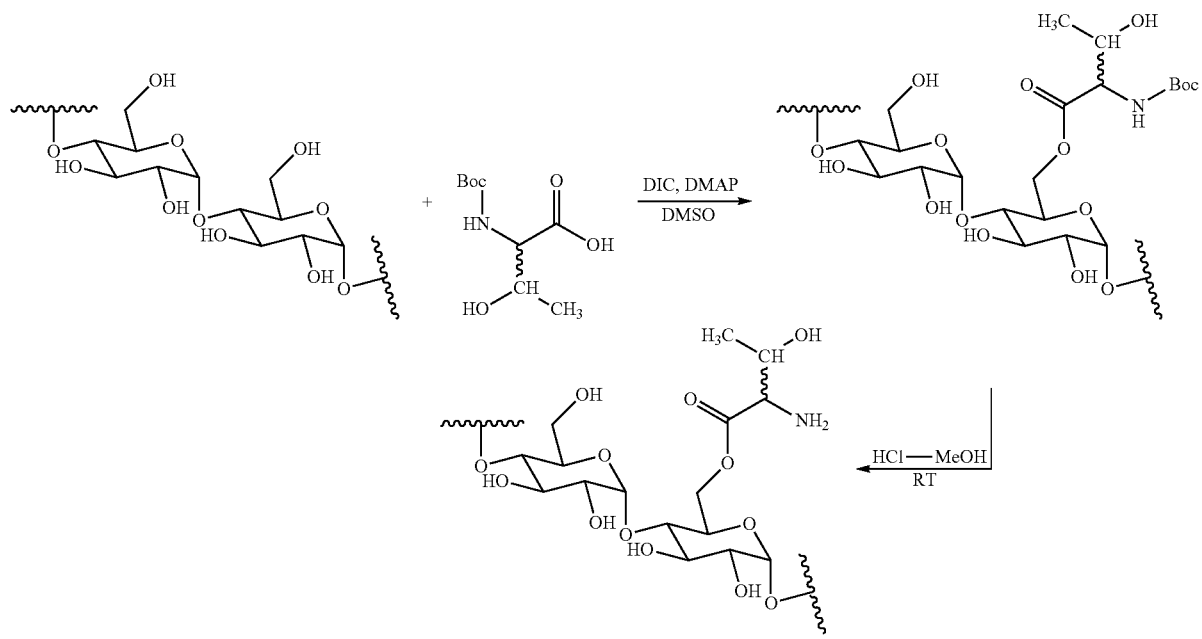

EXAMPLE 3

As shown in the reaction scheme below, maltodextrin is dissolved into dimethylsulfoxide (DMSO) and stirred magnetically until fully dissolved at room temperature. N-Boc-ε-caprolactam is added to the DMSO solution, along with an equivalent of a non-nucleophilic base, such as N-methylmorpholine (NMM). This solution is allowed to react for 120 minutes. The caprolactam-modified polysaccharide can be purified using dialysis in deionized water in SpectraPor dialysis tubing. Lyophilization will yield the dried polymer. The t-butylcarboxyl (Boc) protecting group can be removed with acid hydrolysis using hydrochloric acid in methanol in an organic solvent. The final polymer can be dialyzed again to remove the cleaved protecting group and solvents, followed by lyophilization to achieve the final modified polysaccharide.

What is claimed is:

1. An implantable or injectable biomedical article, the article comprising a polymeric matrix formed from a composition comprising a hydrophobic poly-α(1→4)glucopyranose polymer comprising:
   a poly-α(1→4)glucopyranose portion and
   a pendent group pendent from the poly-α(1→4)glucopyranose portion, the pendent group comprising a hydrocarbon segment comprising one or more carbon atoms and a hydroxyl or an amine group that is present at a terminus of the pendent group.

2. The biomedical article of claim 1 wherein the hydrocarbon segment comprises a branched, cyclic, or linear $C_2$-$C_{18}$ hydrocarbon group.

3. The biomedical article of claim 2 wherein the hydrocarbon segment comprises a branched, cyclic, or linear $C_2$-$C_{12}$ hydrocarbon group.

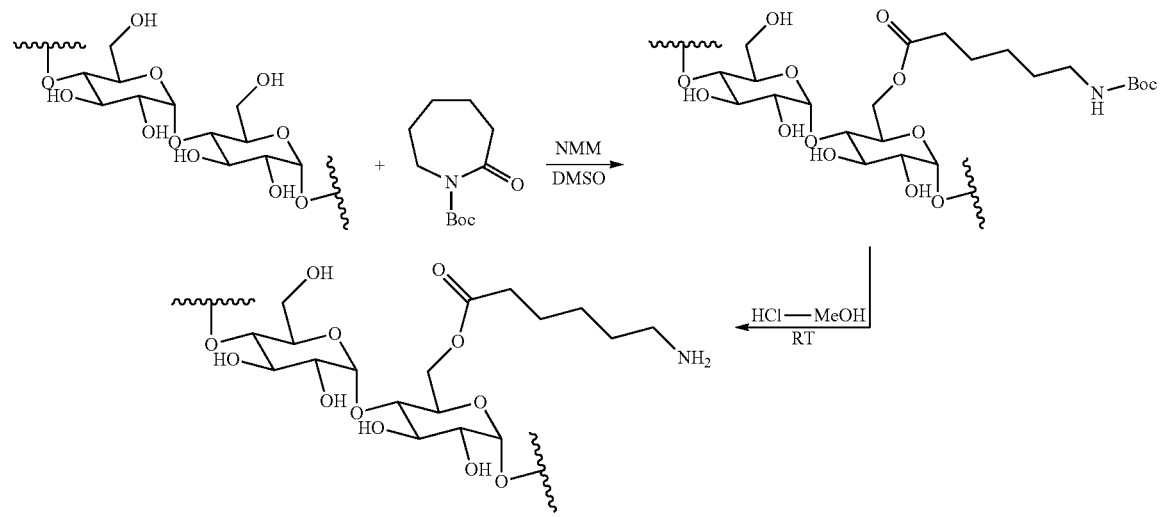

4. The biomedical article of claim 3 wherein the hydrocarbon segment comprises a branched, cyclic, or linear $C_4$-$C_8$ hydrocarbon group.

5. The biomedical article of claim 1 wherein the pendent groups are pendent from primary hydroxyl group positions, or primary and secondary hydroxyl group positions, on the poly-α(1→4)glucopyranose portion.

6. The biomedical article of claim 1 wherein the hydrophobic poly-α(1→4)glucopyranose polymer comprises an amine group that is present at a terminus of the pendent group.

7. The biomedical article of claim 1, wherein the hydrophobic poly-α(1→4)glucopyranose polymer comprises a hydroxyl group that is present at a terminus of the pendent group.

8. The biomedical article of claim 1 wherein the poly-α(1→4)glucopyranose portion comprises glucopyranose monomeric units and the pendent groups are linked to the monomeric units via linking groups comprising an ester group.

9. The biomedical article of claim 1 wherein the poly-α(1→4)glucopyranose portion and the hydroxyl or amine groups are present at a weight to molar ratio in the range of 1 gram: 0.5 mmol to 1 gram: 18 mmol, respectively.

10. The biomedical article of claim 1 wherein the hydrophobic poly-α(1→4)glucopyranose polymer has a hydrophobic portion comprising the hydrocarbon segments, and the hydrophobic portion and the hydroxyl or amine groups are present at a weight to molar ratio in the range of 1 gram: 2 mmol to 1 gram: 15 mmol, respectively.

11. The biomedical article of claim 1 wherein the hydrophobic poly-α(1→4)glucopyranose polymer comprises monomeric units of formula I:

[M¹]-[L¹]-[H¹]—[X¹] 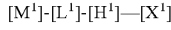

wherein $M_1$ is a monomeric unit of the poly-α(1→4)glucopyranose portion, $X^1$ is the hydroxyl or amine group, $H^1$ is the hydrocarbon segment, and $L^1$ is a linking group;
or of formulas I and II, wherein formula II is:

[M²]-[L²]-[H²] 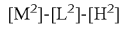

and $M^2$ is a monomeric unit of the poly-α(1→4)glucopyranose portion, $H^2$ is a hydrocarbon segment, and $L^2$ is a linking group.

12. The biomedical article of claim 11 wherein the linkage between [M¹]-[L¹] is derived from a primary hydroxyl group position of [M¹].

13. The biomedical article of claim 11 wherein $L^1$ and/or $L^2$ is a linking group independently selected from an ester group, an ester carbonate group, or a silyl ether group.

14. The biomedical article of claim 1 wherein the hydrophobic poly-α(1→4)glucopyranose polymer comprises monomeric units of formula III:

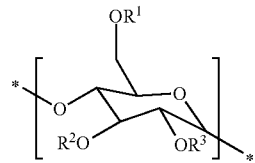

wherein one or more of $R^1$, $R^2$, and/or $R^3$ is $R^4R^5R^6$, wherein $R^4$ is —C(O)—, —C(O)O—, or —C(O)N—, $R^5$ is a divalent linear, branched, or cyclic alkyl radical, and $R^6$ is —OH or —NH$_2$ and for any of $R^1$, $R^2$, or $R^3$ that is not $R^4R^5R^6$ then $R^1$, $R^2$, and/or $R^3$ is —H, or $R^{10}R^{11}$ wherein $R^1$ is —C(O)—, —C(O)O—, or —C(O)N—, and $R^{11}$ is a monovalent linear, branched, or cyclic alkyl radical.

15. The biomedical article of claim 14 wherein $R^5$ is a $C_4$-$C_8$ divalent linear, branched, or cyclic alkyl radical.

16. The biomedical article of claim 15 wherein $R^5$ is a $C_4$, $C_5$, or $C_6$ divalent linear or branched alkyl radical.

17. The biomedical article of claim 1 wherein the hydrophobic poly-α(1→4)glucopyranose polymer has a molecular weight in the range of 5 kDa to 1000 kDa.

18. The biomedical article of claim 17 wherein the hydrophobic poly-α(1→4)glucopyranose polymer has a molecular weight in the range of 25 kDa to 500 kDa.

19. The biomedical article of claim 1, wherein the hydrophobic poly-α(1→4)glucopyranose polymer is covalently bonded to a second article material via reaction of the amine or hydroxyl group.

20. The implantable or injectable biomedical article of claim 1, wherein the polymeric matrix comprises a bioactive agent.

21. A method for treating a medical condition, the method comprising a step of implanting or injecting the biomedical article of claim 1 into a subject.

22. A hydrophobic poly-α(1→4)glucopyranose polymer comprising:
a poly-α(1→4)glucopyranose portion and
pendent groups that are pendent from the poly-α(1→4) glucopyranose portion, the pendent groups comprising a hydrocarbon segment comprising one or more carbon atoms and a hydroxyl or an amine group that is present at a terminus of the pendent group.

* * * * *